United States Patent [19]

Sciarra

[11] Patent Number: 5,303,711
[45] Date of Patent: Apr. 19, 1994

[54] NON-INVASIVE CONTINUOUS BLOOD PRESSURE MONITORING SYSTEM

[76] Inventor: Michael J. Sciarra, 55 Cove Rd., Southhampton, N.Y. 11968

[21] Appl. No.: 727,074

[22] Filed: Jul. 9, 1991

[51] Int. Cl.$^5$ .............................................. A61B 5/00
[52] U.S. Cl. .................................. 128/680; 128/681; 128/687
[58] Field of Search .................. 128/677, 680-686; 364/413.03

[56] References Cited

U.S. PATENT DOCUMENTS

| 4,880,013 | 11/1989 | Chio ................................. 128/681 |
| 5,099,853 | 3/1992 | Uemura et al. ...................... 128/681 |

OTHER PUBLICATIONS

Strong, Biophysical Measurements, Oregon, Tektronix, Inc., 1973, pp. 100-108.
de Jong MD, Tepaske MD, Ros PhD, de Lange MD, PhD. "Non-invasive Continuous Blood Pressure Measurements With The Cortronic APM 770: An Unfortunate Application of Computing Power," VU academisch Ziekenhuis, Amsterdam, The Netherlands.
Chaffee and Lytle, Basic Physionlogy and Anatomy, Philadelphia, J. B. Lippincott Company, 1980, pp. 376-378.
Tardy, Perret, Waeber and Brunner, "Noninvasive Assessment of Arterial Compliance-Pressure Curves, Proc. of 4th European Meeting on Hypertension, Ricerca Scientif. Perman. 76, 862, 1989".
Perrett, Waeber, Tardy, Meister, Burnier, and Brunner, "Compliance-Pressure Curves of the Radial Artery in Normal Subjects Under Prolonged Administration of Atenolol, Isinopril, Nitrendipine and Placebo", Proc. of 4th European Meeting on Hypertension, Ricerca Scientif. Perman. 76, 676, 1989.
Cromwell, Weibell, and Pfeiffer, Biomedical Instrumentation and Measurements, New Jersey, Prentice Hall, 1980, pp. 163-167.
Gesses and Baker, Principles of Applied Biomedical Instrumentation, New York, John Wiley and Sons, 1975, pp. 362-366.
Jorfeldt, MD, "Measurement of Skeletal Muscle Blood Flow in Humans: Plethsmorgraphic, Bolus and Continuous Infusion Techniques," American Journal of Cardiology, 1988; 62:25E-29E.

Primary Examiner—Lee S. Cohen
Assistant Examiner—R. Nasser
Attorney, Agent, or Firm—Curtis, Morris & Safford

[57] ABSTRACT

Apparatus for the continuous non-invasive monitoring of blood is disclosed which includes an inflatable cuff, transducers for detecting blood volume changes in the blood by detecting changes in pressure in the cuff, and a central processing unit which converts the detected blood volume changes to a measurement of blood pressure and a CRT display for displaying the pressures in a readable format.

6 Claims, 6 Drawing Sheets

NON-INVASIVE CONTINUOUS BLOOD PRESSURE MONITORING SYSTEM

The present invention relates to a non-invasive device for the continuous measurement and monitoring of blood pressure.

BACKGROUND OF THE INVENTION

Central blood pressure has traditionally been measured by the insertion of a hollow needle or catheter into a functioning artery. The needle tip is kept clear of clotting blood by a small amount of an anti-coagulant such as hepperin or another similar compound that inhibits clotting of the blood. A tube is connected from the needle and any entrapped air is vented by way of a valve to the atmosphere. Another port on the valve connects with a traditional pressure sensor device. This sensor outputs a direct current voltage that can be calibrated to pressure.

The disadvantages of such invasive blood pressure monitoring systems include the necessity of an anticoagulant, which is extremely dangerous in bleeding patients, hemophiliacs, and small infants, and cross contamination. In addition, finding a patentable artery to be catheterized may be difficult or impossible. Moreover, a frequent result of such invasive procedures is the destruction of the artery at the point of entrance of the catheter. In view of these problems with invasive blood pressure monitoring systems physicians and others have sought to develop blood pressure measurement systems that are non-invasive, easily set up, and do not require constant attention to infusion rates and patentability.

Previous devices such as those offered by Dynamap, Siemens, Datascope, and other manufacturers utilize an oscillometric method for obtaining blood pressure at specific intervals. i.e. every 3 to 10 minutes. This method operates on the empirical correlation between actual blood pressure and the point at which heart sounds (Korotkoff sounds) are heard in an artery as pressure is released from an occluded artery. Typically the artery is occluded by pressurizing a cuff containing an internal air bladder that is wrapped about the arm or leg. As the air is released from the cuff the initial Korotkoff sounds heard correspond to the blood turbulence that is produced as the artery begins to open and blood starts to resume its flow through the artery. This is the systolic or high point of the blood pressure. As the artery opens further turbulence diminishes, heart sounds get lower in intensity, and the diastolic or low point is noted. Conventionally, the mean blood pressure is usually about the average of the two or slightly lower i.e., the mean pressure is at the level of $\frac{1}{3}$ of the difference between the diastolic and systolic values.

The disadvantages of the oscillometric approach is that relatively infrequent readings of pressure are obtained when compared to the continuous blood pressure reading obtained from the "A" line arterial method. Continuous readings are mandatory in some operations and certainly desirable in most. If an attempt is made to cycle these "occlusive" pump up monitors too frequently, i.e. less than 3 minutes apart, nerve trauma and permanent damage can result to the limb involved.

Another method of monitoring blood pressure is to utilize the occlusive method for obtaining the initial readings and then to monitor arterial pulsations at a much lower cuff pressure i.e. 20 to 40 mm hg. In one such system, a sensor is placed on the wrist and adjusted by means of a screw to optimize position over the radical artery in the wrist. The sensor monitors the pulsatility of that artery based on the calibration of a standard occlusive measurement. Other systems rely on pulsatile information from an artery, but utilize the brachial artery in the lower upper arm near the elbow. Such systems determine the patient blood pressure by the initial occlusive measurements, i.e. diastolic, mean, systolic, and apply or assign these measured pressures to the trough, $\frac{1}{3}$ above trough, and peak respectively of the very much lower amplitude pulsations measured from the low pressure cuff sensor. Then various "corrective" factors and scaling algorithms are employed, based on empirical data, to bring the calculations into line with measurements obtained by the invasive A method. As a result, the system continuously monitors pressure variations in the low pressure cuff sensor and continuously calculates an actual pressure based on initial occlusive measurements and its internal algorithms. Applicant believes that the use of pulsatile amplitude measurement as a sole basis for on line continuous computation of the vital sign of blood pressure is dangerous, produces reversed trends, and can lead to the administration of medication that is the opposite of that required for critical and nominal care in controlling blood pressure.

One disadvantage of the use of pulsatile measurement based on initial occlusive determination arises from the fact that the stress/strain curve for the arterial wall is a complex function. If the artery were looked at alone in space, it would still be complex since its walls are comprised of several layers, some of which are smooth muscle that are susceptible to the sympathetic nervous system responses and can react to various stimuli from the body. These vasoconstrictor fibers surrounding the major arterial and venous blood vessels can greatly change the resistance, and compliance or elasticity of the measured artery. Obviously, if the elasticity of the pulsating, measured artery were to change, the amplitude of the pulsations could change also. An example of what happens when this occurs demonstrates the limitations of the pulsatile amplitude method of continuous pressure measurement.

It is known that when peripheral resistance increases the impulses from the medullary vasomotor center to the vasoconstrictor fibers mentioned above increase in rate. This is known to raise arterial pressure and is in fact the primary means that the body utilizes to regulate pressure. As the fibers constrict about their artery, its compliance, elasticity, and pulsatile ability decreases past a certain pressure point (different for all individuals but relatively low in patients that are compromised with hypertension, i.e. (calcified, hard, or clogged vessels)). This effect will cause a lowering of pulsatility for a rise in pressure. This is exactly the opposite of what is supposed to happen according to the pulsatile measurement technique. The pulsatile technique is based on the premise that if the amplitude is increasing, then the pressure is increasing. However, the converse is also true, i.e. that as peripheral resistance goes lower making the arterial wall more compliant, the pulsatility will increase. This erroneously is interpreted by monitors utilizing the pulsatile method as an increase in pressure when, in actuality, the pressure is going down.

Another disadvantage of the pulsatile measurement technique arises because peripheral changes in vessel resistance also produce blood volume changes in the arm or leg. Any change in volume will cause a loss of calibration with respect to the original occlusive reference. For example if more blood enters a fixed volume i.e., the upper arm, the skin acts like a balloon being stretched. As more blood enters the arm, the force of this interarm pressure becomes greater, acting as a constricting force vector on any pulsations of the vessels in the arm aimed back at the center of the vessel. Thus, as interstitial fluid, or blood, increases in the appendage, the ability of the vessels to pulsate diminishes. The pulsatile measurement technique detects this and a pressure decrease which unfortunately is the opposite of what is actually occurring, since pressure in the limb is obviously increasing.

Still further, the non linear relationship of the arterial stress/strain curve can, as the limited working range of the pulsatile method moves up or down on this curve, produce trends opposite that of what is actually taking place. These are caused whenever cardiac output, i.e. volume or peripheral resistance changes occur. These changes occur frequently under anesthesia, intubation, and operating procedures.

Finally the indigenous signal to noise ratio is very low for the desired pulsatile measurements. The problem is that the power spectrum of the typical arterial pulse as acquired by the non-invasive pressure transducers is the same as the muscle and motion artifacts in many cases. Therefore, they are inseparable in either the time or frequency domains. No amount of software or signal processing can restore the data during these often occurring situations. The data is, therefore, discontinuous in many instances, e.g., during an operation or muscle tremor, when it is most needed.

The above described difficulties render the pulsatile measurement technique useful only in those few patients who are not undergoing any physiological change and who have excellent arterial compliance not compromised by vascular hypertension or disease. There are few patients that have these qualities for any length of time useful in realistic monitoring situations.

It is an object of the present invention to provide a more non-invasive method and apparatus for continuously monitoring patient blood pressure.

It is another object of the present invention to provide accurate and continuous blood pressure readings.

Another object of the invention is to provide for continuous blood pressure readings by a method and apparatus which is readily attached to a patient.

In accordance with the present invention blood pressure is measured non-invasively, i.e. without penetration into the body, on a continuous basis. Continuous is defined herein as a moment by moment collection of data as distinguished from intermittent or other devices operating at fixed time intervals. The invention is also designed to overcome the disadvantages of the beforementioned pulsatile amplitude systems.

The apparatus includes a pressure cuff adapted to be placed about a patient's limb. The cuff is connected to a pressure transducer and is initially used to establish systolic and diastolic pressure values by occlusion of the limb. Pressure in the cuff is then decreased to below venous pressure, e.g. 10 mmhg, while the transducer produces pulsatile (A.C.) and absolute (D.C.) output signals. The central processing unit to which the transducer is connected calibrates the AC signal by assigning the previously measured systolic and diastolic pressure values to the peak and trough of the A.C. signal. The D.C. signal is representative then of the mean arterial pressure as the limb expands and contracts due to the increase or decrease in blood volume associated with increasing and decreasing blood pressures. Variations in the amplitude of the AC component of the transducer signal are used as an indication of the absolute value of the systolic peak and diastolic trough about the mean and are not used to calculate the mean.

The above, and other objects features and advantages of this invention will be apparent to those skilled in the art from the following detailed description of an illustrative embodiment thereof when read in connection with the accompanying drawings, where:

Figure 1:
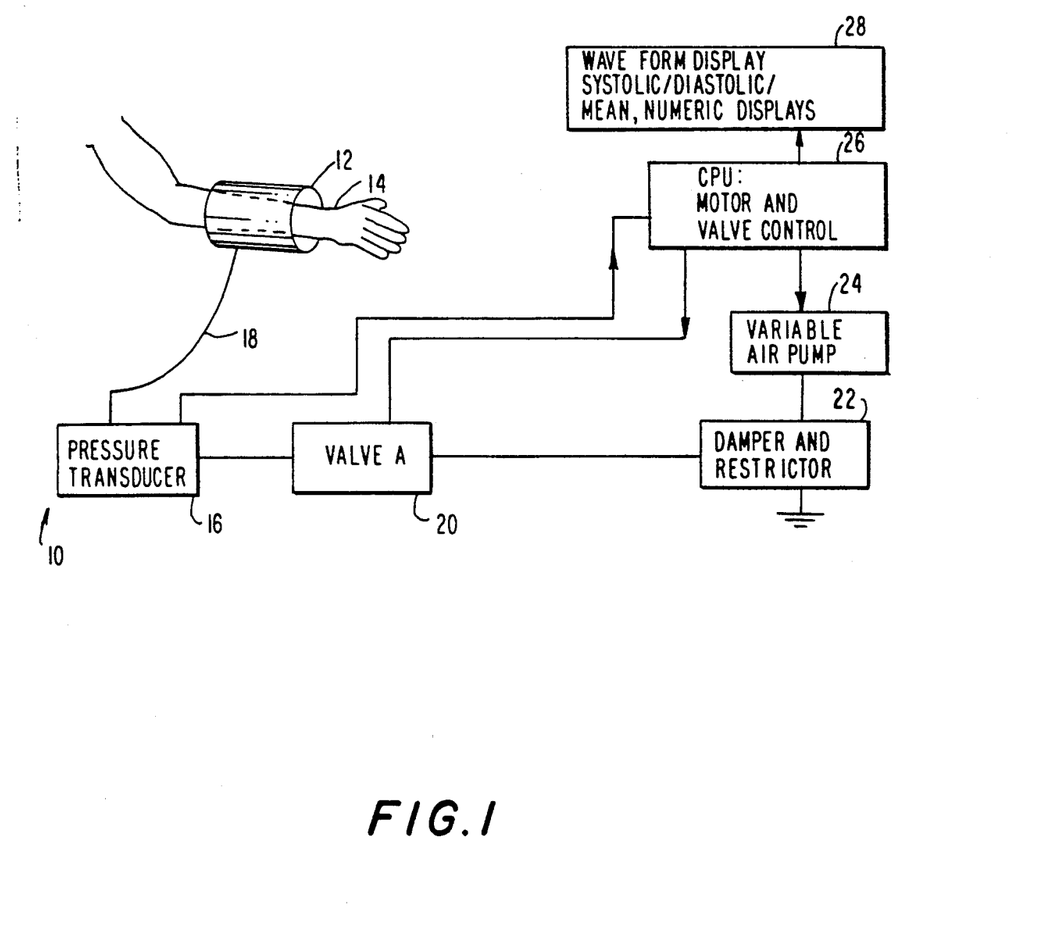
FIG. 1 is a schematic view of a blood pressure monitor according to the present invention.
Figure 2A:
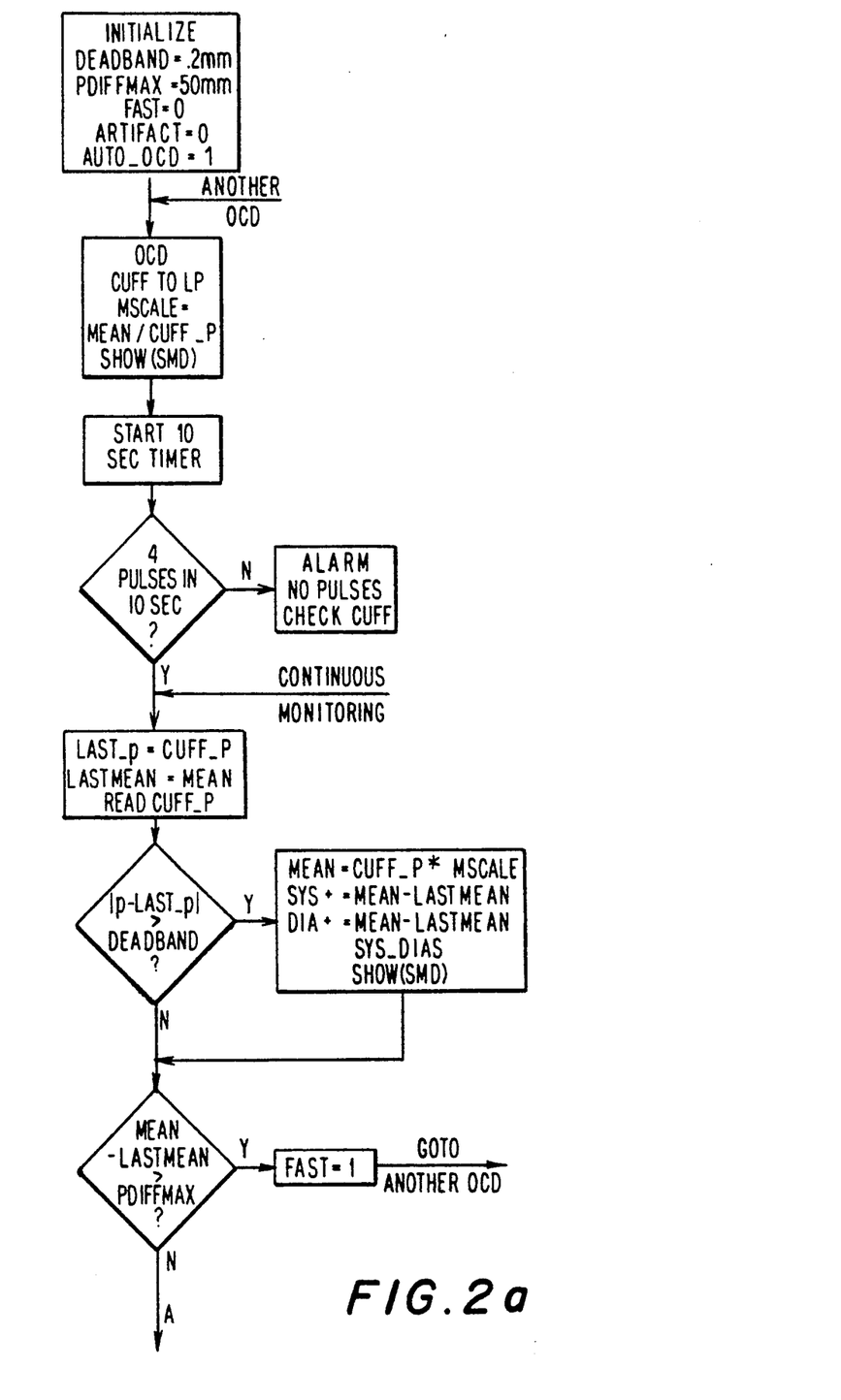
FIG. 2a-2e constitute a flow diagram describing the process steps performed by the CPU of the apparatus to calculate a continuous blood pressure reading.
Figure 2B:
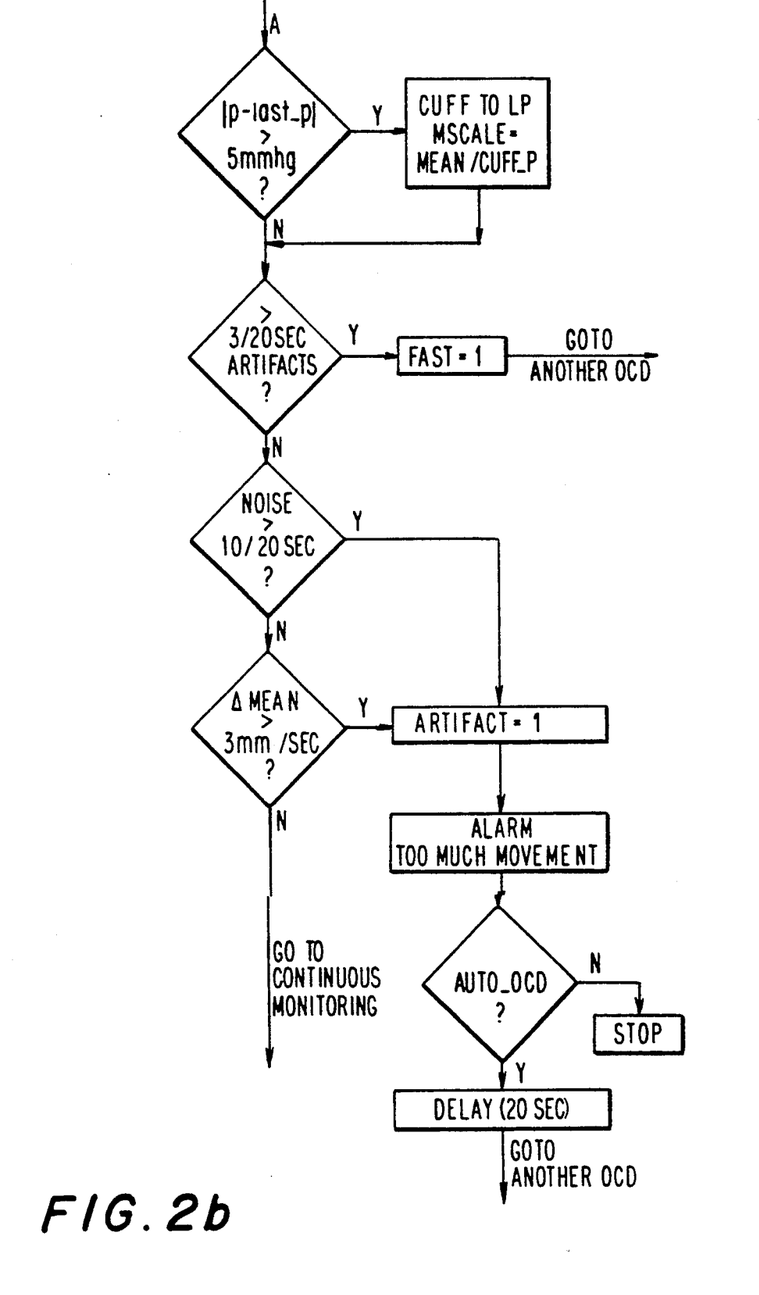
Figure 2C:
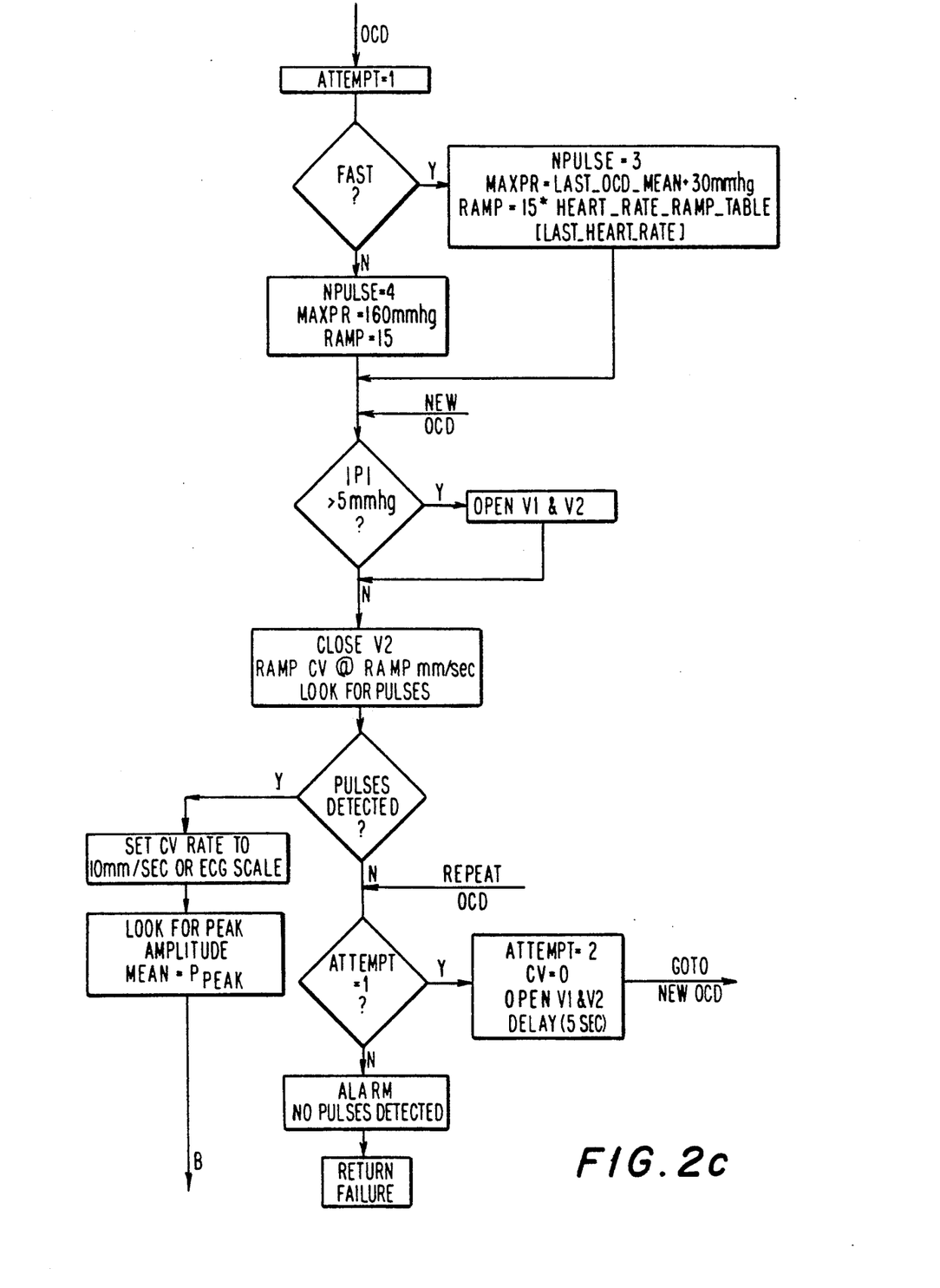
Figure 2D:
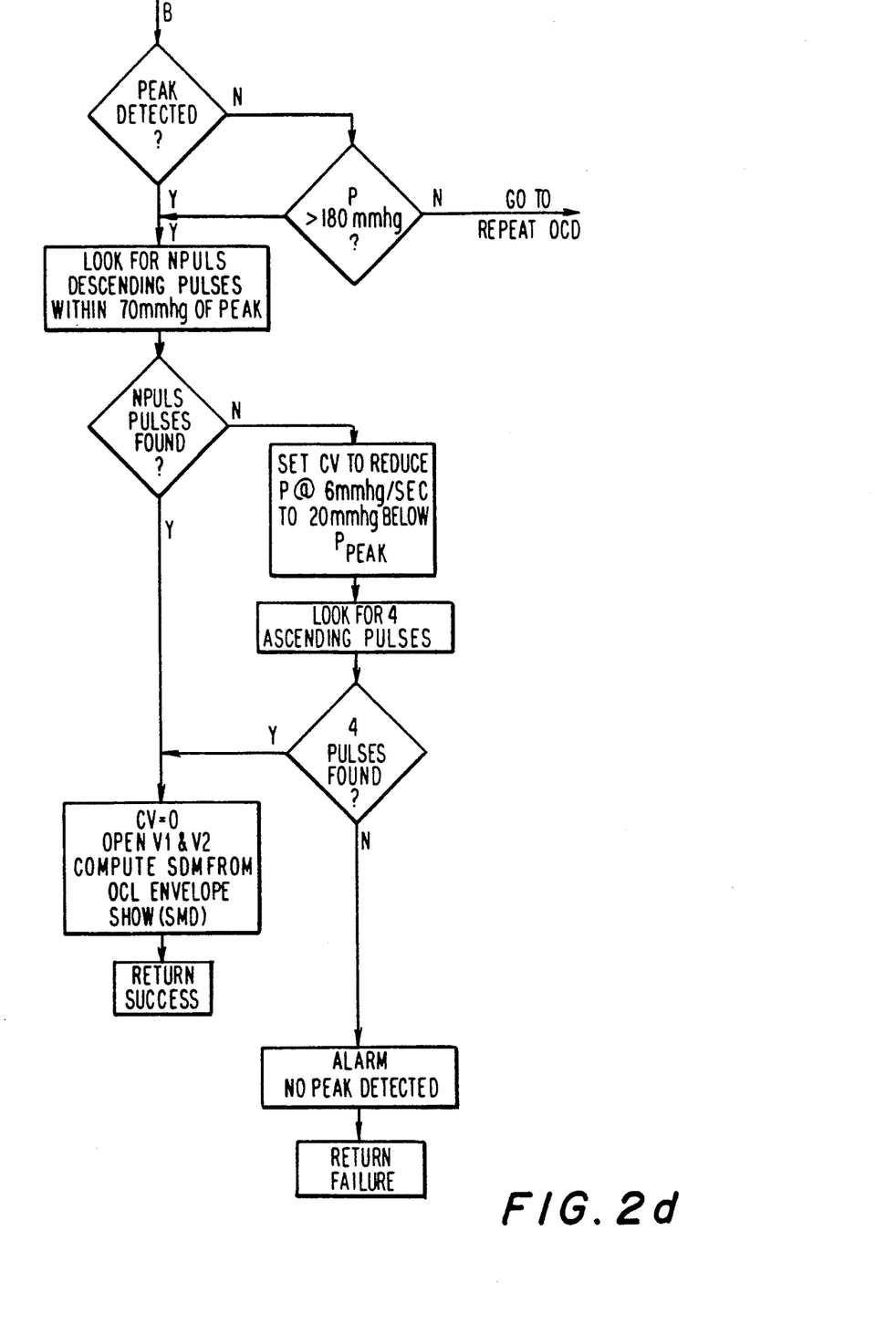
Figure 2E:
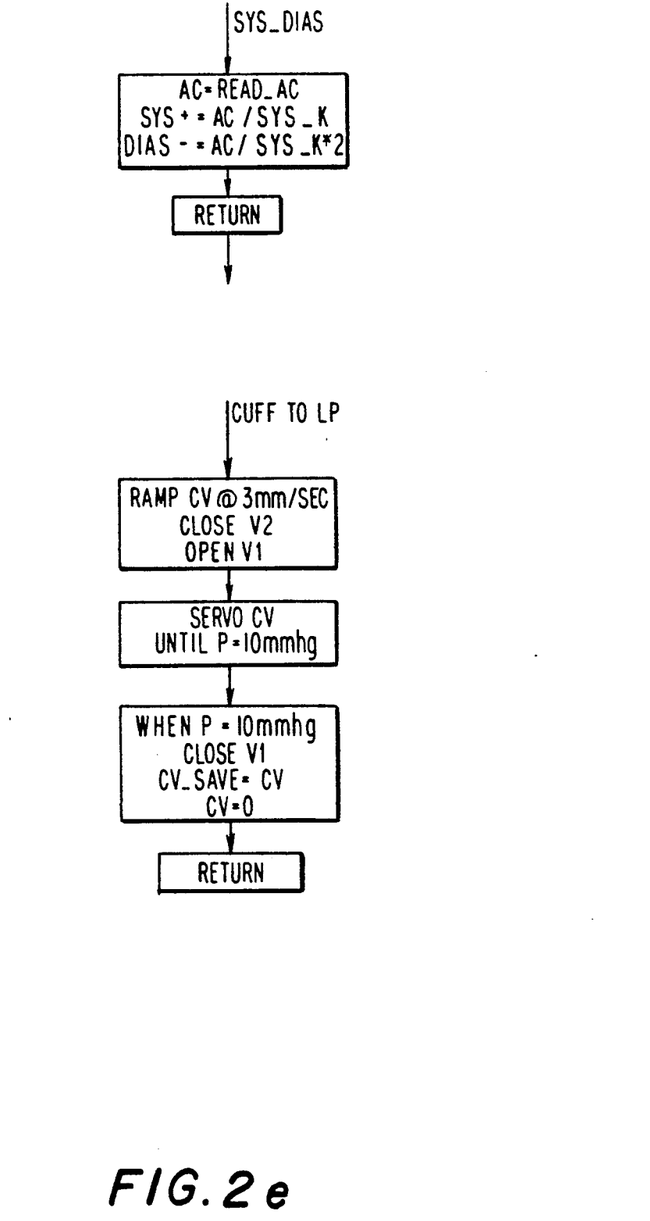

Referring now to the drawing in detail, and initially to FIG. 1, a non-invasive blood pressure monitor 10 according to the present invention is illustrated.

The apparatus 10 includes an inflatable cuff 12, of conventional construction, which is wrapped about a patient's limb 14 and inflated to slightly above systolic pressure by pumping up slowly. The cuff is connected to a pressure transducer 16 through a pressure line 18 which is, in turn, connected through a valve 20, damper and restrictor 22, to an air pump 24. The latter is connected to the central processing unit 26 of the apparatus which includes a CRT display 28 or the like. When the cuff is positioned on the patient and the apparatus turned on, the pre-programmed CPU operates the pump to inflate the cuff to an occlusion pressure. The systolic and diastolic points are detected by a microphone or the actual measurements of pulsations at the output of the pressure transducer, or the like, associated with the transducer in the usual manner as is conventional with the occlusive method, and their values are assigned and stored in the memory of the CPU.

Cuff 12 is then deflated to a fixed pressure below venous pressure, i.e. below 20 mmhg. in most adults and below 7 mmhg in neonates and infants. For example, for a typical adult the pressure in the cuff is reduced to 10 mmhg. The cuff pressure is then monitored carefully. The transducer monitors the pressure in the cuff and produces an A.C. signal corresponding to the peaks and troughs of cuff pressure and a continuous D.C. signal representing the absolute value of pressure in the cuff. No attempt is made to correct or cycle the pressure about the 10 mmhg initial set point. The CPU assigns the 10 mmhg point as the mean computed blood pressure from the occlusive measurement (i.e. a value which is at ⅓ of the difference between systolic and diastolic pressures). The initial peak and trough are calibrated (i.e. assigned) with the values representing systolic and diastolic pressure respectively.

Unlike the previously described pulsatile method, which tries to correlate amplitude changes after an initial OCD (occlusive cuff determination) with systolic/mean/diastolic (SMD) values, the present invention uses the actual DC pressure of the cuff as the limb expands and contracts due to the increase in blood volume associated with increased pressures and the decreased volume associated with pressures that are declining to represent the actual value of mean arterial pressure.

The measurement of blood volume changes is an old one applied through the art of plethysmography. It has been used principally to measure the outflow of blood from the limbs as an indicator for deep thrombosis on the veins and arteries. This old technique demonstrates the non linear and logarithmic relationship of the arterial elasticity curve.

The transducer, air pump and valves of the present invention are of conventional known construction and may be the same components as used in plethysmography. In the present invention however the DC information derived by the transducer from the cuff pressure is used as a means to relate the relative changes in the DC pressure data from the cuff, which is related to volume changes in the limb, to the actual mean blood pressure. It has been shown and accepted by the medical community that if there is a change in the blood volume in the limb, the pressure in that limb is also changing and is directly related. See Geddes and Baker, *Principles of Applied Biomedical Instrumentation*, John Wiley and Sons, 1975, pp362-366.

The amplitude excursion of variations of the AC component of the signal produced by the transducer are used in this invention as an indication of the absolute value of the systolic peak and diastolic trough about the mean which, as described above, is represented by the static cuff pressure and its change from the initial OCD value of, in this example, 10 mmhg. The AC amplitude components are used as an indication of any change in the spread or separation in mmhg. of the systolic and diastolic peaks and are not utilized in the mean pressure calculation in any way.

In another embodiment of this method a separate photo reflectance sensor can be utilized to detect the AC component by shining a high intensity light preferably infrared onto the skin and then measuring the amount of light that is reflected back a short distance from the incident rays. This will be a function of blood perfusion which varies with every heart beat. The waveform is notably less sensitive to motion artifacts when compared with the method of acquiring the pulsatile waveform (AC component) directly from the low pressure cuff. The disadvantage of having a second sensor in some instances may be overcome by the signal to noise ratio advantage.

In another embodiment a strain gauge type of transducer can be used to accomplish the volume change measurement that the system is based on. This is accomplished by utilizing two strain gauges separated by a fixed distance on the limb, e.g. several inches, and observing the circumferential changes produced as the limb fills and empties of blood according to pressure changes in that limb. Two gauges are used to negate any individual motion of the gauges due to artifact and their total contributions are averaged. This overcomes some of disadvantage of measuring volume from only one circumferential site. It can be easily seen that the circumferential change is a response to a volumetric change in the limb and can therefore be utilized in a pressure calculation as volume changes occur primarily due to pressure changes in the vascular network of the limbs. Preferably, as depicted illustratively in FIGS. 2a-2e, the CPU 26 controls valve 20 to open and close to increase or decrease pressure in the cuff upon the detection of artifacts or unusual events. For example, the valve, can be opened to let air in or out of the cuff when the cuff pressure, during continuous monitoring, is observed to rise within a time that is inconsistent with physiological response times. This is called gross motion artifact. It is accompanied by a rise or fall of the static pressure outside the possible physiological bounds of known pressure changes.

More specifically, if the limb the cuff is attached to is relocated to an arm board during surgery from a position tucked close to the body, there will be two immediate and easily detected phenomena. First, a motion artifact of extremely large amplitude will be present during this time and will be detected as a sharp increase in pressure by the computer. Second, the cuff static pressure (in our example 10 mmhg.) will be seen to go rapidly up, e.g. from 10 mmhg to 50 mmhg. within 500 ms or less. This is an impossibility physiologically and so, as artifact, likewise be detected and identified by the CPU. These two combinations of events (but not limited to this combination) will be evaluated and weighted by the software (shown in FIGS. 2a-2e) to determine if any adjustments to the cuff static pressure or to the pressures being displayed are in order. If for example the cuff static pressure after repositioning is different or the same, the following will happen.

1. SP (static pressure)=SAME

If the time for the entire event was less than some value, e.g. less than 1 second, then no correction would occur.

If the event time exceeded 1 second (but not limited to 1 second, as it may be determined that 5 seconds or 10 seconds etc. may be representative), the CPU would operate the pump 24 and valve A to perform a new OCD to reestablish and confirm the baseline mean reference. In other words, the CPU recalibrates the system if the event was too long to rely on the initial calculation, or to safely assume that nothing happened during the repositioning interval to the patient's vascular system.

2. SP=UNEQUAL

In this event, the algorithm evaluates how rapidly the event caused a pressure rise in the cuff and determines if this is within physiological response times or is due to motion or repositioning artifact, as previously described. If SP went up or down without motion artifact detection, and was within physiologic realities, then a new patient pressure update would be displayed reflecting the monitor's accepting new valid data.

If the SP change due to the event was in the presence of artifact for more than a certain percentage of the time of the event (e.g. 50% but not limited to 50%), and the SP change was within physiologic limits, then a new OCD would be initiated.

If the SP change due to the event was in the presence of artifact, and within physiologic realities, but for 50% of the total time for the event (in this example), then the computer would allow the data as valid and display a new patient pressure accordingly without performing a new OCD.

The CPU program shown in FIGS. 2a-2e is also designed to adjust the system to events not necessarily derived from patient motion artifact. For example, if the static cuff pressure, without motion artifact detection, should rise or fall at a rate inconsistent with predetermined physiologic constants stored in the CPU memory, then an OCD will be initiated 2 times in an attempt to reestablish calibration. Failing to recalibrate, a message will be displayed on CRT 28 alerting the operator that monitoring has ceased. In addition, if the static cuff pressure should rise or fall without motion artifact within accepted physiologic rates, then the displayed values for pressure will be updated accordingly.

Finally, if the SP in the cuff should exceed +/−5 mmhg. (but not limited to) from the initial continuous SP (i.e. 10 mmhg in this example) while monitoring, then valve 20 will open to re-establish the original static cuff pressure of 10 mmhg. No new data or numeric update will occur during this time. The repressurizing event is timed so as not to exceed 2 seconds and is accomplished typically within 500 ms., i.e. within one heart beat at 60 bpm. This is done so that neither too low a pressure is in the cuff, nor too high a pressure (above venous occlusion) is presented to the patient. Data remains unchanged as the system knows that it itself has initiated any artifacts or pressure changes it detects as a result of the repressurization routine.

The system of the present invention operates similarly with the strain gauge method except that the valve and pump are inoperative after the OCD and the use of a valve to govern cuff pressure is necessary. The disadvantages of the strain gauge system are the lack of a precisely repeatable commercially available circumferential gauge, and the necessity for wires to be connected to the patient adding complexity and potential for shock that occurs with any patient wire interface design.

Although the invention has been described with reference to the illustrative embodiment, it is to be understood that the invention is not limited to that precise embodiment and that various changes and modifications may be effected therein without departing form the scope or spirit of this invention.

What is claimed is:

1. Apparatus for the continuous non-invasive monitoring of blood pressure comprising, an inflatable cuff adapted to surround a limb of a patient, transducer means for detecting pressure in the cuff and producing separate A.C. and D.C. signals respectively representing a) peaks and troughs of cuff pressure and b) static pressure in the cuff; means for initially inflating the cuff to a pressure sufficient to occlude blood flow in the limb, means for detecting systolic and diastolic blood pressure points of the patient; means for calculating mean blood pressure of the patient based on the detected systolic and diastolic pressures; means for reducing the pressure in the cuff to a predetermined pressure lower than diastolic occlusion pressure, means for assigning to the DC signal from the transducer means produced by said lower predetermined pressure the calculated mean blood pressure of the patient and means for monitoring the D.C. signal produced while the pressure in the cuff remains lower than said diastolic occlusion pressure to produce an output reading of the patient's blood pressure.

2. Apparatus for the continuous non-invasive monitoring of blood pressure comprising an inflatable cuff adapted to surround a limb of a patient, means for initially inflating said cuff to a pressure sufficient to occlude blood flow in said limb; means for detecting systolic and diastolic blood pressure points of the patient and for sensing separation between the systolic and diastolic pressures; means for calculating a mean blood pressure of the patient as a function of the detected systolic and diastolic pressures; means for reducing the pressure in the cuff to a predetermined pressure lower than diastolic occlusion pressure; means for producing an A.C. signal and a D.C. signal repectively representing a) the peaks and troughs of cuff pressure and b) the mean pressure in the cuff following the reduction of pressure in said cuff to said predetermined pressure; means for determining the separation of the peaks and troughs of said A.C. signal; means for comparing said separation of the peaks and troughs to said separation between the systolic and diastolic pressures and means for utilizing the comparison and the D.C. signal to produce an indication of the blood pressure of the patient.

3. Apparatus for the continuous non-invasive monitoring of blood pressure comprising an inflatable cuff adapted to surround a limb of a patient; means for initially inflating the cuff to a pressure sufficient to occlude blood pressure points of the patient; means for detecting systolic and diastolic pressures of the patient and for calculating mean blood pressure as a function thereof; controllable valve means opened to reduce the pressure in the cuff to a predetermined pressure lower than diastolic occlusion pressure and subsequently closed to permit the cuff pressure to vary as the patient's pressure varies; means for producing a D.C. signal representing the mean pressure in the cuff following the reduction of pressure in said cuff to said predetermined pressure; means for assigning the calculated mean blood pressure to said D.C. signal when the pressure in the cuff has been reduced to said predetermined pressure; and means for monitoring said D.C. signal as an indication of the patient's blood pressure after the pressure in the cuff has been reduced to said predetermined pressure and said valve means remains closed.

4. The apparatus of claim 3, further comprising means for storing the monitored D.C. signal; means for sensing when the monitored D.C. signal changes from its initial value by more than a predetermined amount; means responsive to said sensing means for opening said valve means to restore the pressure in the cuff to said predetermined pressure; and means for inhibiting the monitored D.C. signal from being stored while the pressure in the cuff is restored.

5. The apparatus of claim 4, further including means for producing an A.C. signal representing peaks and troughs of cuff pressure; means for determining the separation between said peaks and troughs after said valve means is closed and said predetermined pressure is reached; and means for monitoring changes in said separation to indicate changes in the systolic and diastolic pressures of the patient.

6. Apparatus for the non-invasive monitoring of blood pressure comprising an inflatable cuff adapted to surround a limb of a patient, transducer means for detecting pressure in the cuff and producing A.C. signals representing peaks and troughs of cuff pressure; means for initially inflating the cuff to a pressure sufficient to occlude blood flow in the limb and for thereafter reducing the pressure in the cuff to a predetermined pressure lower than a diastolic occlusion pressure; means for determining a separation between the peaks and troughs of said A.C. signal following the reduction of pressure in said cuff to said predetermined pressure; means for monitoring changes in said separation between the peaks and troughs; and means for indicating changes in said separation.

* * * * *